United States Patent [19]

Tsai et al.

[11] Patent Number: 6,110,849

[45] Date of Patent: Aug. 29, 2000

[54] THERMOPLASTIC COMPOSITION INCLUDING POLYETHYLENE OXIDE

[75] Inventors: Fu-Jya Tsai; Brian T. Etzel, both of Appleton, Wis.

[73] Assignee: Kimberly-Clark Worlwide, Inc., Neenah, Wis.

[21] Appl. No.: 08/994,183

[22] Filed: Dec. 19, 1997

[51] Int. Cl.⁷ .............................. B32B 5/16; B32B 27/02; B32B 27/32; B32B 27/36

[52] U.S. Cl. .......................... 442/394; 442/118; 428/357; 428/480; 428/483; 525/165; 525/166; 525/176; 525/177; 525/231; 525/240

[58] Field of Search ................................... 428/357, 480, 428/483; 442/394, 118; 525/165, 166, 176, 231, 177, 240

[56] References Cited

U.S. PATENT DOCUMENTS

| | | | |
|---|---|---|---|
| 3,946,089 | 3/1976 | Furukawa et al. | 260/857 PG |
| 4,617,235 | 10/1986 | Shinonome et al. | 428/374 |
| 4,649,920 | 3/1987 | Rhum | 128/335.5 |
| 4,818,542 | 4/1989 | DeLuca et al. | 424/491 |
| 5,120,701 | 6/1992 | Brand et al. | 502/350 |
| 5,290,494 | 3/1994 | Coombes et al. | 264/41 |
| 5,330,768 | 7/1994 | Park et al. | 424/501 |
| 5,413,797 | 5/1995 | Khan et al. | 424/489 |
| 5,417,712 | 5/1995 | Whittaker et al. | 606/232 |
| 5,476,909 | 12/1995 | Kim et al. | 525/408 |
| 5,514,380 | 5/1996 | Song et al. | 424/426 |
| 5,589,545 | 12/1996 | Ramachandran et al. | 525/184 |

FOREIGN PATENT DOCUMENTS

| | | | |
|---|---|---|---|
| 0 241 178 A1 | 10/1987 | European Pat. Off. | A61K 9/70 |
| 0351 949 | 7/1988 | European Pat. Off. | |
| 0 693 528 | 1/1996 | European Pat. Off. | |
| 7-133511 | 5/1995 | Japan | D01F 8/12 |
| WO 90/05522 A1 | 5/1990 | WIPO | A61K 9/22 |
| WO 92/04923 A1 | 4/1992 | WIPO | A61L 15/01 |
| WO 93/10731 A1 | 6/1993 | WIPO | A61F 13/00 |

OTHER PUBLICATIONS

Patent Abstracts of Japan, JP 09–111537 (Chikyu Kankyo Sangyo Gijutsu Kenkyu Kiko), Apr. 28, 1997.

American Society for Testing Materials (ASTM) Designation: D1238–95, "Standard Test Method for Flow Rates of Thermoplastics by Extrusion Plastomer," pp. 273–281, published Jan. 1996.

Good, Robert J. and Robert J. Stromberg, Editors, Surface and Colloid Science–Experimental Methods, vol. II, Plenum Press, 1979, pp. 31–91.

Derwent World Patent Database abstract of GB 1,289,305 A: Description of Imperial Chemical Ind., "Polyesters."

Derwent World Patent Database abstract of JP 05–093,316 A: Description of Unitika Ltd (Nira), "Biodegradable Conjugated Fibre For Construction, Fiserhy, Etc."

Derwent World Patent Database abstract of JP 05–093,317 A: Description of Unitika Ltd (Nira), "Crimpable Biodegradable Conjugated Fibre For Napkins, Etc."

Derwent World Patent Database abstract of JP 05–093,318 A: Description of Unitika Ltd (Nira), "Biodegradable Conjugated Fibre For Nonwoven Fabric For Sanitary Goods, Fishery, Etc."

Derwent World Patent Database abstract of JP 06–022,995 A: Description of Yokoi T, "Water–Soluble Contraceptive Article Having High Cleanliness And High Barrier Against Viruses."

Derwent World Patent Database abstract of JP 06–206,320 A: Description of Unitika Ltd (Nira), "Biodegradable Conjugate Short Fibre For Nonwoven Fabric For Sanitary Items."

Derwent World Patent Database abstract of JP 06–207,323 A: Description of Unitika Ltd (Nira), "Biodegradable Latent Crimping Conjugate Core–Sheath Type Long Fibre."

Derwent World Patent Database abstract of JP 06–207,324 A: Description of Unitika Ltd (Nira), "Biodegradable Conjugate Core–Sheath Type Long Fiber."

Derwent World Patent Database abstract of JP 06–212,548 A: Description of Unitika Ltd (Nira), "Biodegradable Latent Crimpable Conjugate Short Fibre For Nonwoven Fabric."

Derwent World Patent Database abstract of JP 06–248,552 A: Description of Daiwabo Creat Co. Ltd., "Biodegradable Fibre Composition."

Derwent World Patent Database abstract of RU 2,048,299 C1: Description of N.N. Melentev et al., "Synthesis Of Composite Materials From Poly–Dispersed Systems."

Derwent World Patent Database abstract of WO 92/11844 A1: Description of H.E. Auer et al., "Sustained Release Delivery Systems For Proteins Or Peptide(s)."

Derwent World Patent Database abstract of WO 93/00050 A1: Description of B.S. Isaacs et al., "Composition For Stimulating Growth Of Bone Or Cartilage."

Derwent World Patent Database abstract of WO 94/12158 A1: Description of H. Auer et al., "Growth Hormone Microsphere Controlled Release Formulation."

Chemical Abstract 108(4)26944j: Description of Hani Younes et al., "Morphological Study Of Biodegradable PEO/PLA Block Copolymers," *J. Biomed. Mater. Res.*,1987, vol. 21, No. 11, pp. 1301–1316.

(List continued on next page.)

*Primary Examiner*—Vivian Chen
*Attorney, Agent, or Firm*—Jones & Askew, LLP

[57] ABSTRACT

A thermoplastic composition that comprises a mixture of a polyethylene oxide polymer, a polyolefin polymer, a polyester polymer, and, optionally, a compatibilizer for the polymers. One embodiment of such a thermoplastic composition is a mixture of polyethylene oxide polymer, poly(lactic acid) polymer, and polyethylene polymer. The thermoplastic composition is capable of being extruded into fibers that may be formed into nonwoven structures that may be used in a disposable absorbent product intended for the absorption of fluids such as body fluids.

45 Claims, No Drawings

OTHER PUBLICATIONS

Chemical Abstract 109(24)215956w: Description of Daniel Cohn et al., "A Selectively Biodegadable Vascular Graft," *Prog. Biomed. Eng.*, 1988, vol. 5, No. Polym. Med. 3, pp. 73–79.

Chemical Abstract 110(8)63680g: Description of H. Younes et al., "Biodegradable PELA Block Copolymers: In Vitro Degradation And Tissue Reaction," *Biomater., Artif. Cells, Artif. Organs*, 1988, vol. 16, No. 4, pp. 705–719.

Chemical Abstract 110(4)29042r: Description of Daniel Cohn et al., "Biodegradable PEO/PLA Block Copolymers," *J. Biomed. Mater. Res.*, 1988, vol. 22, No. 11, pp. 993–1009.

Chemical Abstract 111(16)134863c: Description of K.J. Zhu et al., "Super Microcapsules," *J. Polym. Sci., Part A: Polym. Chem.*, 1989, vol. 27, No. 7, pp. 2151–2159.

Chemical Abstract 112(8)62574e: Description of Daniel Cohn et al., "Compositional And Structural Analysis of PELA Biodegradable Block," *Biomaterials*, 1989, vol. 10, No. 9, pp. 466–474.

Chemical Abstract 115(8)72647g: Description of Xiaobing Zou et al., "Carbon–13 NMR Relaxation Study On Poly-(Ethylene Oxide)–Polyllactide Star–Block Copolymer," *Fenxi Ceshi Tongbao*, 1990, vol. 9, No. 5, pp. 18–26.

Chemical Abstract 119(24)250977g: Description of Chitoshi Nakafuku et al., "Melting And Crystallization Of Poly(L– Lactic Acid) And Poly(Ethylene Oxide) Binary Mixture," *Polym. J. (Tokyo)*, 1993, vol. 25, No. 9, pp. 909–917.

Chemical Abstract 121(4)36571t: Description of Chitoshi Nakafuku, "High Pressure Crystallization Of Poly(L–Lactic Acid) In A Binary Mixture with Poly(Ethylene Oxide)," *Polym. J. (Tokyo)*, 1994, vol. 26, No. 6, pp. 680–687.

Chemical Abstract 123(20)258609s: Description of C.L. Yue et al., "Miscibility And Degradability Of Poly(Lactic Acid)/ Poly(Ethylene Oxide)/Poly(Ethylene Glycol) Blends," *Polym. Prepr. (Am. Chem. Soc., Div. Polym. Chem.)*, 1995, vol. 36, No. 1, pp. 418–419.

Chemical Abstract 124(2)9578f: Description of I. Rashkov et al., "Synthesis, Characterization, and Hydrolytic Degradation Of PLA/PEO/PLA Triblock Copolymers With Short Poly(L–Lactic Acid) Chains," *Macromolecules*, 1996, vol. 29, No. 1, pp. 50–56.

Chemical Abstract 124(4)30530u: Description of S.M. Li et al., "Synthesis, Characterization, and Hydrolytic Degradation Of PLA/PEO/PLA Triblock Copolymers With Long Poly(L–Lactic Acid) Blocks," *Macromolecules*, 1996, vol. 29, No. 1, pp. 57–62.

Chemical Abstract 125(8)87792f: Description of Kwang– Suk Kim et al., "Effect Of PLA–PEO Block Copolymers On The Compatibility Of PLA/PEO Blends," *Pollimo*, 1996, vol. 20, No. 3, pp. 497–505.

Chemical Abstract 125(8)95740c: Description of T. Kissel et al., "Parenteral Protein Delivery Systems Using Biodegradable Polyesters Of ABA Block Structure, Containing Hydrophobic Poly(Lactide–Co–Glycolide) A Blocks And Hydrophilic Poly(Ethylene Oxide) B Blocks," *J. Controlled Release*, 1996, vol. 39, No. 2,3, pp. 315–326.

Chemical Abstract 125(10)115695w: Description of Chitoshi Nakafuku, "Effects Of Molecular Weight On The Melting And Crystallization Of Poly(L–Lactic Acid) In A Mixture With Poly(EthyleneOxide)," *Polym. J. (Tokyo)*, 1996, vol. 28, No. 7, pp. 568–575.

Chemical Abstract 125(12)144076b: Description of C.L. Yue et al., "Miscibility And biodegradability Of Poly(Lactic Acid)/poly(Ethylene Oxide) And Poly(Lactic Acid)/Polyethylene Glycol Blends," *Annu. Tech. Conf.–Soc. Plast. Eng.*, 1996, vol. 54, No. 2, pp. 1611–1615.

Chemical Abstract 125(16)204203c: Description of Michaella Vittaz et al., "Effect Of PEO Surface Density On Long–Circulating PLA–PEO Nanoparticles Which Are Very Low Complement Activators," *Biomaterials*, 1996, vol. 17, No. 16, pp. 1575–1581.

Chemical Abstract 125(16)204264y: Description of Y.K. Choi et al., "Protein Release From Microspheres Of Star– Shaped PEO–PLA Block Compolymers," *Proc. Int. Symp. Controlled Release Bioact. Mater.*, 1996, vol. 23, pp. 349–350.

THERMOPLASTIC COMPOSITION INCLUDING POLYETHYLENE OXIDE

FIELD OF THE INVENTION

The present invention relates to a the thermoplastic compositions The thermoplastic compositions are capable of being extruded into fibers that may be formed into nonwoven structures that may be used in a disposable absorbent product intended for the absorption of fluids such as body fluids.

DESCRIPTION OF THE RELATED ART

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Polyethylene oxide is a known material and has been used widely in a variety of applications. However, the processing of polyethylene oxide into a fiber, a film, or other extrudable or nonwoven structures has proven to be a significant challenge. This challenging task has been found to be particularly acute when trying to use polyethylene oxide in a fiber making process. Such processing difficulty is due, in part, to the fact that commercially-available polyethylene oxide typically comes in a powder form and is predominately available in high molecular weight versions, typically ranging in a weight average molecular weight from over 100,000 to 20,000,000.

Such a physical form or properties of the polyethylene oxide has been found to negatively impact the processing of the polyethylene oxide in several ways. First, any material, including polyethylene oxide, in a powder form is generally more difficult to process in terms of feeding and extrusion as compared to a material in a pelletized form, such as is typically encountered, for example, with polyolefins. Second, the high molecular weight of the polyethylene oxide typically results in significant entanglement of the polyethylene oxide polymer chains during certain processing techniques, such as extrusion. An extruder being used in such a situation will typically require a very large torque to feed the high molecular weight material through it which typically results in a pronounced "elastic-retraction" property of the molten fiber being processed which generally results in the molten fiber resisting being drawn down as it exits a spinneret attached to the extruder. These factors generally result in a very poor melt strength of the resultant fiber and make fiber spinning impracticable. Third, polyethylene oxide has a very low melting temperature, generally about 65° C., which makes the polyethylene oxide difficult to solidify during quenching and which causes process difficulties due to the stickiness of fiber prepared from the polyethylene oxide.

In addition, polyethylene oxide is generally a water soluble polymer. As such, even if one were able to prepare fibers from polyethylene oxide, such fibers would have a limited usefulness in applications in which the fibers were to be insulted with a liquid such as water, urine, blood, or menses. Thus, it would be desirable to be able to make a fiber comprising polyethylene oxide which was not instantly water soluble but instead exhibited a delayed solubility in, for example, water or other aqueous liquids.

It is therefore an object of the present invention to provide a thermoplastic composition comprising polyethylene oxide which exhibits improved processability properties and desirable solubility properties.

It is also an object of the present invention to provide a thermoplastic composition comprising polyethylene oxide which may be easily and efficiently formed into a fiber.

It is also an object of the present invention to provide a thermoplastic composition comprising polyethylene oxide which is suitable for use in preparing nonwoven structures.

It is also an object of the present invention to provide a fiber or nonwoven structure that is readily degradable in the environment.

SUMMARY OF THE INVENTION

The present invention concerns a thermoplastic composition that is desirably substantially biodegradable and yet which is easily prepared and readily processable into desired final structures, such as fibers or nonwoven structures.

One aspect of the present invention concerns a thermoplastic composition that comprises a mixture of a first component, a second component, and a third component.

One embodiment of such a thermoplastic composition comprises a mixture of a polyethylene oxide polymer, a polyolefin polymer, and an aliphatic polyester polymer, wherein the thermoplastic composition exhibits desired properties.

In another aspect, the present invention concerns a fiber prepared from the thermoplastic composition wherein the fiber exhibits desired properties.

In another aspect, the present invention concerns a nonwoven structure comprising a fiber prepared from the thermoplastic composition.

One embodiment of such a nonwoven structure is a backsheet useful in a disposable absorbent product.

In another aspect, the present invention concerns a disposable absorbent product comprising a nonwoven structure comprising a fiber prepared from the thermoplastic composition.

DETAILED DESCRIPTION OF THE PREFERRED EMBODIMENTS

The present invention is directed to a thermoplastic composition which includes a first component, a second component, and a third component. As used herein, the term "thermoplastic" is meant to refer to a material that softens when exposed to heat and generally returns to its original condition when cooled to room temperature.

The first component in the thermoplastic composition is a polyethylene oxide polymer. Suitable polyethylene oxide polymers are known and may be obtained, for example, from Union Carbide Corporation of Danbury, Conn.

The polyethylene oxide polymer suitable for use in the present invention is desirably water soluble. As used herein, a material will be considered to be water soluble when it substantially dissolves in excess water to form a solution, thereby losing its initial form and becoming essentially molecularly dispersed throughout the water solution. As a general rule, a water-soluble material will be free from a substantial degree of crosslinking, as crosslinking tends to render a material water insoluble.

As used herein, the term "water-insoluble" is meant to refer to a material that, when exposed to an excess of water, substantially disperses but does not dissolve into the solution. As such, a water-insoluble material generally retains its original identity or physical structure, but in a highly dispersed state and must have sufficient physical integrity to resist flow and fusion with neighboring materials.

It is generally desired that the polyethylene oxide polymer exhibit a weight average molecular weight that is effective for the thermoplastic composition to exhibit desirable melt strength, fiber mechanical strength, fiber spinning, and water responsiveness properties. In general, if the weight average molecular weight of a polyethylene oxide polymer is too high, this represents that the polymer chains may become heavily entangled which may result in a thermoplastic composition comprising that polyethylene oxide polymer being difficult to process. Conversely, if the weight average molecular weight of a polyethylene oxide polymer is too low, this represents that the polymer chains are not entangled enough which may result in a thermoplastic composition comprising that polyethylene oxide polymer exhibiting a relatively weak melt strength, making high speed processing very difficult. Thus, polyethylene oxide polymers suitable for use in the present invention exhibit weight average molecular weights that are beneficially between about 100,000 to about 20,000,000, more beneficially between about 150,000 to about 10,000,000, and suitably between about 200,000 to about 8,000,000. The weight average molecular weight for polymers or polymer blends can be determined using a method as described in the Test Methods section herein.

It is generally desired that the polyethylene oxide be present in the thermoplastic composition in an amount effective to result in the thermoplastic composition exhibiting desired properties. If the polyethylene oxide is present in the thermoplastic composition in too small of an amount, the thermoplastic composition, or a material prepared from such a thermoplastic composition, will generally exhibit poor solubility or dispersibility properties such as, for example, being too slowly dispersible in water or other aqueous liquids, thereby limiting the use the thermoplastic composition, or a material prepared from such a thermoplastic composition, in applications such as disposable absorbent products where the disposable absorbent product is desired to be flushable. In contrast, if the polyethylene oxide is present in the thermoplastic composition in too large of an amount, the thermoplastic composition will generally exhibit poor extrusion processability properties represented, for example, by exhibiting too high of an apparent viscosity during processing at conditions, for example, of about 200° C. and a shear rate of about 1000 seconds$^{-1}$ as well as the thermoplastic composition, or a material prepared from such a thermoplastic composition, being too quickly dispersible in water or other aqueous liquids, thereby limiting the use of the thermoplastic composition, or a material prepared from such a thermoplastic composition, in applications such as disposable absorbent products.

Therefore, the polyethylene oxide will be present in the thermoplastic composition of the present invention in a weight amount that is beneficially between about 5 weight percent to about 60 weight percent, more beneficially between about 10 weight percent to about 55 weight percent, and suitably between about 20 weight percent to about 50 weight percent, wherein all weight percents are based on the total weight amount of the polyethylene oxide polymer, polyolefin polymer, aliphatic polyester polymer, and, optionally, a compatibilizer present in the thermoplastic composition. The compositional ratio of the various components in the thermoplastic composition is generally important to obtain the desired properties of the thermoplastic composition, or a material prepared from such a thermoplastic composition, such as biodegradability, thermal stability, processability, and dispersibility in water.

The processing of polyethylene oxide into a fiber, a film, or other extrudable or nonwoven structures has, however, proven to be a significant challenge. This challenging task has been found to be particularly acute when trying to use polyethylene oxide in a fiber making process. Such processing difficulty is due, in part, to the fact that commercially-available polyethylene oxide typically comes in a powder form and is predominately available in high molecular weight versions, typically ranging in a weight average molecular weight from over 100,000 to 20,000,000.

Such a physical form or properties of the polyethylene oxide has been found to negatively impact the processing of the polyethylene oxide in several ways. First, any material, including polyethylene oxide, in a powder form is generally more difficult to process in terms of feeding and extrusion as compared to a material in a pelletized form, such as is typically encountered, for example, with polyolefins. Second, the high molecular weight of the polyethylene oxide typically results in significant entanglement of the polyethylene oxide polymer chains during certain processing techniques, such as extrusion. An extruder being used in such a situation will typically require a very large torque to feed the high molecular weight material through it which typically results in a pronounced "elastic-retraction" property of the molten fiber being processed which generally results in the molten fiber resisting being drawn down as it exits a spinneret attached to the extruder. These factors generally result in a very poor melt strength of the resultant fiber and make fiber spinning impracticable. Third, polyethylene oxide has a very low melting temperature, generally about 65° C., which makes the polyethylene oxide difficult to solidify during quenching and which causes process difficulties due to the stickiness of fiber prepared from the polyethylene oxide.

In addition, polyethylene oxide is generally a water soluble polymer. As such, even if one were able to prepare fibers from polyethylene oxide, such fibers would have a limited usefulness in applications in which the fibers were to be insulted with an aqueous liquid such as water, urine, blood, or menses. Furthermore, polyethylene oxide is generally a hydrophilic polymer, typically exhibiting a water in air contact angle of less than about 40 degrees.

As used herein, the term "hydrophilic" refers to a material having a contact angle of water in air of less than 90 degrees. In contrast, as used herein, the term "hydrophobic" refers to a material having a contact angle of water in air of at least 90 degrees. The general subject of contact angles and the measurement thereof is well known in the art as, for example, in Robert J. Good and Robert J. Stromberg, Ed., in "Surface and Colloid Science—Experimental Methods", Vol. II, (Plenum Press, 1979), particularly pages 63–70.

It would therefore be desirable to be able to make a fiber comprising polyethylene oxide which is more easily processable and which also was not instantly water soluble or dispersible but instead exhibits a delayed solubility or dispersibility in water or other aqueous liquids. As such, the present research work has combined the polyethylene oxide polymer with a polyolefin polymer, the second component in the thermoplastic composition of the present invention. This is because polyolefin polymers are, first, generally relatively easy to process under typical extrusion conditions and, second, polyolefin polymers are generally hydrophobic, typically exhibiting a water in air contact angle of greater than about 100 degrees. Thus, a combination of a polyethylene oxide polymer and a polyolefin polymer should result in a thermoplastic composition that is more easily processable and which exhibits more desirable water solubility or dispersibility properties in water as compared to the use of polyethylene oxide polymer alone.

Polyolefins are known to those skilled in the art. Any polyolefin capable of being fabricated into an article is believed suitable for use in the present invention. Exemplary of polyolefins suitable for use in the present invention are the homopolymers and copolymers comprising repeating units formed from one or more aliphatic hydrocarbons, including ethylene, propylene, butene, pentene, hexene, heptene, octene, 1,3-butadiene, and 2-methyl-1,3-butadiene. Suitably, the polyolefin is a polyethylene or a polypropylene polymer. The polyolefins may be high or low density and may be generally linear or branched chain polymers. Methods of forming polyolefins are known to those skilled in the art. Suitable polyolefin polymers are known and may be obtained, for example, from Himont USA, Inc. of Wilmington, Del., under the designations PF301 polypropylene, PF304 polypropylene, and PF305 polypropylene, and from Exxon Chemical Company, of Houston, Tex., under the designation ESCORENE™ 3445 polypropylene.

It is generally desired that the polyolefin polymer suitable for use in the present invention exhibit a melting temperature that is beneficially between about 100° C. to about 210° C., more beneficially between about 110° C. to about 190° C., and suitably between about 120° C. to about 180° C.

It is generally desired that the polyolefin polymer be present in the thermoplastic composition in an amount effective to result in the thermoplastic composition exhibiting desired properties. If the polyolefin polymer is present in the thermoplastic composition in too small of an amount, the thermoplastic composition will generally exhibit poor extrusion processability properties represented, for example, by exhibiting too high of an apparent viscosity during processing at conditions, for example, of about 200° C. and a shear rate of about 1000 seconds$^{-1}$ as well as the thermoplastic composition, or a material prepared from such a thermoplastic composition, being too quickly dispersible in water or other aqueous liquids, thereby limiting the use of the thermoplastic composition, or a material prepared from such a thermoplastic composition, in applications such as disposable absorbent products where the disposable absorbent product is desired to be flushable. In contrast, if the polyolefin polymer is present in the thermoplastic composition in too large of an amount, the thermoplastic composition, or a material prepared from such a thermoplastic composition, will generally be too slowly dispersible in water or other aqueous liquids, thereby limiting the use the thermoplastic composition, or a material prepared from such a thermoplastic composition, in applications such as disposable absorbent products where the disposable absorbent product is desired to be flushable.

Therefore, the polyolefin polymer will be present in the thermoplastic composition in a weight amount that is beneficially between about 5 weight percent to about 40 weight percent, more beneficially between about 10 weight percent to about 35 weight percent, and suitably between about 15 weight percent to about 30 weight percent, wherein all weight percents are based on the total weight amount of the polyethylene oxide polymer, polyolefin polymer, aliphatic polyester polymer and, optionally, a compatibilizer present in the thermoplastic composition present in the thermoplastic composition.

However, it has been discovered as part of the present research work that using a mixture of only a polyethylene oxide polymer and a polyolefin polymer generally results in a thermoplastic composition that is not readily processable at conditions, for example, of about 200° C. and a shear rate of about 1000 seconds$^{-1}$. While not wishing to be bound hereby, such a lack of processability of a mixture of only a polyethylene oxide polymer and a polyolefin polymer is believed to be due to a large extent to the chemical incompatibility between the polyethylene oxide polymer and the polyolefin polymer since the polyethylene oxide polymer and the polyolefin polymer are not chemically identical and generally exhibit widely divergent water in air contact angle values. Such chemical incompatibility between the polyethylene oxide polymer and the polyolefin polymer generally makes such polymers difficult to effectively mix and prepare as an essentially homogeneous mixture on their own. As such, the present invention generally requires the use of a third component that is generally chemically compatible with each of the polyethylene oxide polymer and the polyolefin polymer so as to allow for the effective preparation and processing of the polyethylene oxide polymer and the polyolefin polymer into a single thermoplastic composition.

Thus, the third component in the thermoplastic composition of the present invention is a polyester polymer. Suitable polyester polymers include, but are not limited to, poly (lactic acid), polybutylene succinate, polybutylene succinate-co-adipate, polyhydroxybutyrate-co-valerate, polycaprolactone, sulfonated polyethylene terephthalate, mixtures of such polymers, or copolymers of such polymers. Polyester polymers typically exhibit a water in air contact angle of about 90 degrees.

In one embodiment of the present invention, it is desired that the polyester polymer used is poly(lactic acid). Poly (lactic acid) polymer is generally prepared by the polymerization of lactic acid. However, it will be recognized by one skilled in the art that a chemically equivalent material may also be prepared by the polymerization of lactide. As such, as used herein, the term "poly(lactic acid) polymer" is intended to represent the polymer that is prepared by either the polymerization of lactic acid or lactide. One reason for the desirability of using a poly(lactic acid) polymer is that poly(lactic acid) polymers are generally hydrolytically degradable, wherein exposure or contact with water generally results in the degrading or breaking apart or decomposition of the poly(lactic acid) polymer, therefore assisting in the substantial degradability of the thermoplastic composition of the present invention, or a material prepared from such a thermoplastic composition.

Lactic acid and lactide are known to be asymmetrical molecules, having two optical isomers referred to, respectively, as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare different polymers that are chemically similar yet which have different properties. In particular, it has been found that by modifying the stereochemistry of a poly(lactic acid) polymer, it is possible to control, for example, the melting temperature, melt rheology, and crystallinity of the polymer. By being able to control such properties, it is possible to prepare a thermoplastic composition and a multicomponent fiber exhibiting desired melt strength, mechanical properties, softness, and processability properties so as to be able to make attenuated, heat-set, and crimped fibers.

Examples of poly(lactic acid) polymers that are suitable for use in the present invention include a variety of poly (lactic acid) polymers that are available from Chronopol Inc., Golden, Colo.

It is generally desired that the polyester polymer exhibit a weight average molecular weight that is effective for the thermoplastic composition to exhibit desirable melt strength, fiber mechanical strength, and fiber spinning properties. In general, if the weight average molecular weight of a particular polymer is too high, this represents that the polymer chains are heavily entangled which may result in a thermoplastic composition comprising that polymer being difficult to process. Conversely, if the weight average molecular weight of a particular polymer is too low, this represents that the polymer chains are not entangled enough which may result in a thermoplastic composition comprising that polymer exhibiting a relatively weak melt strength, making high speed processing very difficult. Thus, polyester polymers suitable for use in the present invention respectively exhibit weight average molecular weights that are beneficially between about 10,000 to about 2,000,000, more beneficially between about 50,000 to about 400,000, and suitably between about 100,000 to about 300,000. The weight average molecular weight for polymers or polymer blends can be determined using a method as described in the Test Methods section herein.

It is also desired that the polyester polymer exhibit a polydispersity index value that is effective for the thermoplastic composition to exhibit desirable melt strength, fiber mechanical strength, and fiber spinning properties. As used herein, "polydispersity index" is meant to represent the value obtained by dividing the weight average molecular weight of a polymer by the number average molecular weight of the polymer. In general, if the polydispersity index value of a particular polymer is too high, a thermoplastic composition comprising that polymer may be difficult to process due to inconsistent processing properties caused by polymer segments comprising low molecular weight polymers that have lower melt strength properties during spinning. Thus, it is desired that the polyester polymer exhibit a polydispersity index value that is beneficially between about 1 to about 15, more beneficially between about 1 to about 4, and suitably between about 1 to about 3. The number average molecular weight for polymers or polymer blends can be determined using a method as described in the Test Methods section herein.

It is generally desired that the polyester polymer be present in the thermoplastic composition in an amount effective to result in the thermoplastic composition exhibiting desired properties. If the polyester polymer is present in the thermoplastic composition in too small of an amount, the thermoplastic composition will generally exhibit poor extrusion processability properties at conditions, for example, of about 200° C. and a shear rate of about 1000 seconds$^{-1}$ as well as generally exhibiting undesirable dispersibility properties in water or other aqueous liquids, thereby limiting the use of such fibers in applications such as disposable absorbent products. In contrast, if the polyester polymer is present in the thermoplastic composition in too large of an amount, the thermoplastic composition will generally exhibit poor extrusion processability properties at conditions, for example, of about 200° C. and a shear rate of about 1000 seconds$^{-1}$ as well as generally exhibiting undesirable dispersibility properties in water or other aqueous liquids, thereby limiting the use of such fibers in applications such as disposable absorbent products.

Therefore, the polyester polymer will be present in the thermoplastic composition in a weight amount that is beneficially between about 5 weight percent to about 70 weight percent, more beneficially between about 10 weight percent to about 60 weight percent, and suitably between about 20 weight percent to about 50 weight percent, wherein all weight percents are based on the total weight amount of the polyethylene oxide polymer, polyolefin polymer, polyester polymer and, optionally, a compatibilizer present in the thermoplastic composition.

It is generally desired that each of the polyethylene oxide polymer, the polyolefin polymer, and the polyester polymer be melt processable. It is therefore desired that the polyethylene oxide polymer, the polyolefin polymer, and the polyester polymer used in the present invention each exhibit a melt flow rate that is beneficially between about 1 gram per 10 minutes to about 600 grams per 10 minutes, suitably between about 5 grams per 10 minutes to about 200 grams per 10 minutes, and more suitably between about 10 grams per 10 minutes to about 150 grams per 10 minutes. The melt flow rate of a material may be determined according to ASTM Test Method D1238-E, incorporated in its entirety herein by reference.

In the present invention, it is desired that the polyethylene oxide polymer and the polyester polymer generally be biodegradable. As a result, the thermoplastic composition of the present invention, comprising the three polymers, either in the form of a fiber or in the form of a nonwoven structure, will desirably be substantially degradable when disposed of to the environment and exposed to air and/or water. As used herein, "biodegradable" is meant to represent that a material degrades from the action of naturally occurring microorganisms such as bacteria, fungi, and algae.

In the present invention, it is also desired that the polyethylene oxide polymer and polyester polymer be compostable. As a result, the thermoplastic composition of the present invention, comprising the three polymers, either in the form of a fiber or in the form of a nonwoven structure, will desirably be substantially compostable when disposed of to the environment and exposed to air and/or water. As used herein, "compostable" is meant to represent that a material is capable of undergoing biological decomposition in a compost site such that the material is not visually distinguishable and breaks down into carbon dioxide, water, inorganic compounds, and biomass, at a rate consistent with known compostable materials.

Either separately or when mixed together, the polyester polymer polymer and the polyolefin polymer are generally hydrophobic. However, it is generally desired that the thermoplastic composition of the present invention, and fibers prepared from the thermoplastic composition, generally be hydrophilic so that such fibers are useful in disposable absorbent products which are insulted with aqueous liquids such as water, urine, menses, or blood. Thus, since polyethylene oxide polymer is generally hydrophilic, it is generally desired that an effective amount of the polyethylene oxide polymer be used in the thermoplastic composition to ensure that the thermoplastic composition or fibers prepared from the thermoplastic composition generally be hydrophilic. Optionally, it has been found possible to use another component as a surfactant in the thermoplastic composition of the present invention in order to achieve the desired hydrophilic properties.

Furthermore, it has been found desirable to improve the processability of the polyethylene oxide polymer, the polyolefin polymer, and the polyester polymer since such polymers are not chemically identical and are, therefore, somewhat incompatible with each other which tends to negatively affect the processing of a mixture of such polymers. For example, the polyethylene oxide polymer, the polyolefin polymer, and the polyester polymer are sometimes difficult to effectively mix and prepare as an essentially homogeneous mixture on their own. Optionally, then, a compatibilizer may be used to aid in the effective preparation and processing of the polyethylene oxide polymer, the polyolefin polymer, and the polyester polymer into a single thermoplastic composition.

As such, in one embodiment of the present invention, a fourth component is used in the thermoplastic composition. Such a fourth component is a compatibilizer for the polyethylene oxide polymer, the polyolefin polymer, and the polyester polymer. Compatibilizers suitable for use in the present invention will generally comprise a hydrophilic section and a hydrophobic section. These sections will generally exist in separate blocks so that the overall compatibilizer structure may be di-block or random block. The compatibilizer functions as a plasticizer to improve the processing of the thermoplastic composition and then serves as a surfactant in a processed fiber or nonwoven structure by modifying the contact angle of the processed material. The hydrophobic portion of the compatibilizer may be, but is not limited to, a polyolefin such as polyethylene or polypropylene. The hydrophilic portion of the compatibilizer may contain ethylene oxide, ethoxylates, glycols, alcohols or any combinations thereof. Examples of suitable compatibilizers include UNITHOX®480 and UNITHOX®750 ethoxylated alcohols, or UNICID® Acid Amide Ethoxylates, all from Petrolite Corporation of Tulsa, Okla.

It is generally desired that the compatibilizer exhibit a weight average molecular weight that is effective for the thermoplastic composition to exhibit desirable melt strength, fiber mechanical strength, fiber spinning, and water responsiveness properties. In general, if the weight average molecular weight of a compatibilizer is too high, the compatibilizer will not blend well with the other components in the thermoplastic composition because the compatibilizer's viscosity will be so high that it lacks the mobility needed to blend. Conversely, if the weight average molecular weight of the compatibilizer is too low, this represents that the compatibilizer will not blend well with the other components and have such a low viscosity that it causes processing problems. Thus, compatibilizers suitable for use in the present invention exhibit weight average molecular weights that are beneficially between about 1,000 to about 100,000, suitably between about 1,000 to about 50,000, and more suitably between about 1,000 to about 10,000. The weight average molecular weight for a compatibilizer can be determined using known methods.

It is generally desired that the compatibilizer exhibit an effective hydrophilic-lipophilic balance ratio (HLB ratio). The HLB ratio of a material describes the relative ratio of the hydrophilicity of the material. The HLB ratio is calculated as the weight average molecular weight of the hydrophilic portion divided by the total weight average molecular weight of the material multiplied by 20. If the HLB ratio value is too low the material will not provide the desired improvement in wettability. Conversely, if the HLB ratio value is too high the material will not blend into the thermoplastic composition because of chemical incompatibility and differences in viscosities with the other components. Thus, compatibilizers suitable for use in the present invention exhibit HLB ratio values that are beneficially between about 10 to about 40, suitably between about 10 to about 20, and more suitably between about 12 to about 16.

It is generally desired that the compatibilizer be present in the thermoplastic composition in an amount effective to result in the thermoplastic composition exhibiting desired properties. The compatibilizer will be present in the thermoplastic composition in a weight amount that is beneficially between about 0 weight percent to about 25 weight percent, suitably between about 0 weight percent to about 20 weight percent, and more suitably between about 5 weight percent to about 15 weight percent, wherein all weight percents are based on the total weight amount of the polyethylene oxide polymer, the polyolefin polymer, and the polyester polymer present in the thermoplastic composition.

While the principal components of the thermoplastic composition of the present invention have been described in the foregoing, such thermoplastic composition is not limited thereto and can include other components not adversely effecting the the desired properties of the thermoplastic composition. Exemplary materials which could be used as additional components would include, without limitation, pigments, antioxidants, stabilizers, surfactants, waxes, flow promoters, solid solvents, plasticizers, nucleating agents, particulates, and materials added to enhance processability of the thermoplastic composition. If such additional components are included in a thermoplastic composition, it is generally desired that such additional components be used in an amount that is beneficially less than about 5 weight percent, more beneficially less than about 3 weight percent, and suitably less than about 1 weight percent, wherein all weight percents are based on the total weight amount of the polyethylene oxide polymer, the polyolefin polymer, and the polyester polymer present in the thermoplastic composition.

The thermoplastic composition of the present invention is generally simply a mixture of the polyethylene oxide polymer, the polyolefin polymer, the polyester polymer and, optionally, a compatibilizer or any additional components. In order to achieve the desired properties for the thermoplastic composition of the present invention, it has been discovered that it is desirable that the polyethylene oxide polymer, the polyolefin polymer, the polyester polymer and, optionally, any compatibilizer remain substantially unreacted with each other such that a copolymer comprising any of the various components is not formed. As such, each of the polyethylene oxide polymer, the polyolefin polymer, the polyester polymer and, if used, the compatibilizer remain distinct components of the thermoplastic composition. In order to determine if the various components remain essentially unreacted, it is possible to use techniques, such as nuclear magnetic resonance and infrared analysis, to evaluate the chemical characteristics of the final thermoplastic composition.

Each of the polyethylene oxide polymer, the polyolefin polymer, the polyester polymer and, optionally, a compatibilizer will generally form separate regions or domains within a prepared mixture forming the thermoplastic composition. However, depending on the relative amounts that are used of each of the various components, an essentially continuous phase may be formed from the component that is present in the thermoplastic composition in a relatively greater amount. In contrast, the components that are present in the thermoplastic composition in a relatively lesser amount may form essentially discontinuous phases, forming separate regions or domains within the continuous phase of the more prevalent component wherein the more prevalent component continuous phase substantially encases the less prevalent components within its structure. As used herein, the term "encase", and related terms, are intended to mean that the more prevalent component continuous phase substantially encloses or surrounds the less prevalent components' separate regions or domains.

In the thermoplastic composition of the present invention, the compatibilizer is believed to perform at least one important function. When the thermoplastic composition is in a molten state, the compatibilizer is believed to function as a process lubricant or plasticizer that facilitates the processing of the thermoplastic composition while increasing the flexibility and toughness of a final product, such as a fiber or a nonwoven structure, through internal modification of the various polymers. While not intending to be bound hereby, it is believed that the compatibilizer replaces the secondary valence bonds holding together the various polymer chains with compatibilizer-to-polymer valence bonds, thus facilitating the movement of the polymer chain segments. This effect is evidenced, for example, in that a generally lower extrusion temperature may be used to process the thermoplastic composition comprising both the three polymers and the compatibilizer as compared to the processing of any of the polymers alone. With this effect, the torque needed to turn an extruder is generally dramatically reduced as compared with the processing of any of the polymers alone.

In one embodiment of the present invention, after dry mixing together the polymers and, optionally, the compatibilizer to form a thermoplastic composition dry mixture, such thermoplastic composition dry mixture is beneficially agitated, stirred, or otherwise blended to effectively uniformly mix the components such that an essentially homogeneous dry mixture is formed. The dry mixture may then be melt blended in, for example, an extruder to effectively uniformly mix the components such that an essentially homogeneous melted mixture is formed. The essentially homogeneous melted mixture may then be cooled and pelletized. Alternatively, the essentially homogeneous melted mixture may be sent directly to a spin pack or other equipment for forming fibers or a nonwoven structure. Other methods of mixing together the components of the present invention are also possible and will be easily recognized by one skilled in the art.

Alternative methods of mixing together the components of the present invention include first mixing together the polyethylene oxide polymer, the polyolefin polymer, and the polyester polymer and then adding the compatibilizer to such a mixture in, for example, an extruder being used to mix the components together. In addition, it is also possible to initially melt mix all of the components together at the same time. Other methods of mixing together the components of the present invention are also possible and will be easily recognized by one skilled in the art.

The process of cooling the extruded thermoplastic composition to ambient temperature is usually achieved by blowing ambient or sub-ambient temperature air over the extruded polymer. It can be referred to as quenching or super-cooling because the change in temperature is usually greater than 100° C. and most often greater than 150° C. over a relatively short time frame (seconds).

It is generally desired that the melting or softening temperature of the thermoplastic composition be within a range that is typically encountered in most process applications. As such, it is generally desired that the melting or softening temperature of the thermoplastic composition beneficially be between about 25° C. to about 350° C., more beneficially be between about 50° C. to about 300° C., and suitably be between about 60° C. to about 200° C.

The thermoplastic composition of the present invention has been found to generally exhibit improved processability properties as compared to, in particular, a thermoplastic composition comprising only the polyethylene oxide polymer or a thermoplastic composition comprising only the polyethylene oxide polymer and the polyolefin polymer. As used herein, the improved processability of a thermoplastic composition is measured as a decline in the apparent viscosity of the thermoplastic composition at a temperature of about 200° C. and a shear rate of about 1000 seconds$^{-1}$, typical industrial extrusion processing conditions. If the thermoplastic composition exhibits an apparent viscosity that is too high, the thermoplastic composition will generally be very difficult to process. In contrast, if the thermoplastic composition exhibits an apparent viscosity that is too low, the thermoplastic composition will generally result in an extruded fiber that has very poor tensile strength.

Therefore, it is generally desired that the thermoplastic composition exhibits an Apparent Viscosity value at a temperature of about 200° C. and a shear rate of about 1000 seconds$^{-1}$ that is beneficially between about 5 Pascal seconds (Pa.s) to about 200 Pascal seconds, more beneficially between about 10 Pascal seconds to about 150 Pascal seconds, and suitably between about 20 Pascal seconds to about 100 Pascal seconds. The method by which the Apparent Viscosity value is determined is set forth below in connection with the examples.

Typical conditions for thermally processing the thermoplastic composition include using a shear rate that is beneficially between about 100 seconds$^{-1}$ to about 50000 seconds$^{-1}$, more beneficially between about 500 seconds$^{-1}$ to about 5000 seconds$^{-1}$, suitably between about 1000 seconds$^{-1}$ to about 3000 seconds$^{-1}$, and most suitably at about 1000 seconds$^{-1}$. Typical conditions for thermally processing the components also include using a temperature that is beneficially between about 100° C. to about 500° C., more beneficially between about 150° C. to about 300° C., suitably between about 175° C. to about 250° C., and suitably about 200° C.

The thermoplastic composition of the present invention is suited for preparing fibers or nonwoven structures that may be used in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the fibers prepared from the thermoplastic composition of the present invention. When used in a disposable absorbent product, it is generally desired that a fiber prepared from the thermoplastic composition of the present invention be hydrophilic and exhibit desired solubility or dispersibility properties in water or other aqueous liquids. In particular, it is generally desired that the thermoplastic composition of the present invention, or a material prepared from such a thermoplastic composition, exhibit a delayed solubility or dispersibility when immersed in water. As used herein, the "delayed" solubility of a sample of a thermoplastic composition, or of a material prepared from such a thermoplastic composition, is intended to represent that the sample exhibits a maximum force point, reflecting the change from water absorption to water dissolution, that occurs at a time greater than about 5 minutes but less than about 2 hours. In contrast, a thermoplastic composition, or of a material prepared from such a thermoplastic composition, that exhibit undesired solubility or dispersibility properties in water or other aqueous liquids can either exhibit too fast or too slow of a solubility or dispersibility in water or other aqueous liquids. As used herein, a sample of a thermoplastic composition, or of a material prepared from such a thermoplastic composition, will exhibit too fast of a solubility or dispersibility in water when the sample exhibits a maximum force point, reflecting the change from water absorption to water dissolution, that occurs at a time less than about 5 minutes. As used herein, a sample of a thermoplastic composition, or of a material prepared from such a thermoplastic composition, will exhibit too slow of a solubility or dispersibility in water when the sample exhibits a maximum force point, reflecting the change from water absorption to water dissolution, that occurs at a time greater than about 2 hours. The water dispersibility of a sample may be determined according to the procedure as described in the Test Methods section herein. The exact timing of the delayed solubility or dispersibility of a thermoplastic composition, or of a material prepared from such a thermoplastic composition, can be affected by the compositional ratios of the components used to prepare the thermoplastic composition.

In one embodiment of the present invention, the thermoplastic composition is formed into a multicomponent fiber. For purposes of illustration only, the present invention will generally be described in terms of a multicomponent fiber comprising only three components. However, it should be understood that the scope of the present invention is meant to include fibers with three or more components. In one embodiment, the thermoplastic composition of the present invention may be used to form the sheath of a multicomponent fiber while a polyolefin, such as polypropylene or polyethylene is used to form the core. Suitable structural geometries for multicomponent fibers include pie shape or side by side configurations.

As used herein, the term "fiber" or "fibrous" is meant to refer to a material wherein the length to diameter ratio of such material is greater than about 10. Conversely, a "non-fiber" or "nonfibrous" material is meant to refer to a material wherein the length to diameter ratio of such material is about 10 or less.

Methods for making fibers are well known and need not be described here in detail. To form a fiber, generally, a thermoplastic composition is extruded and fed to a distribution system where the thermoplastic composition is introduced into a spinneret plate. The spun fiber is then cooled, solidified, and drawn, generally by a mechanical rolls system, to an intermediate filament diameter and collected. Subsequently, the fiber may be "cold drawn" at a temperature below its softening temperature, to the desired finished fiber diameter and is crimped/texturized and cut into a desirable fiber length. Fibers can be cut into relatively short lengths, such as staple fibers which generally have lengths in the range of about 25 to about 50 millimeters and short-cut fibers which are even shorter and generally have lengths less than about 18 millimeters.

When the thermoplastic composition of the present invention is formed into a multicomponent fiber, an exposed surface on at least a portion of the multicomponent fiber will typically be formed from the more prevalent material present in the multicomponent fiber. Such an exposed surface on at least a portion of the multicomponent fiber which will generally permit thermal bonding of the multicomponent fiber to other fibers which may be the same or different from the multicomponent fiber of the present invention. As a result, the multicomponent fiber can then be used to form thermally bonded fibrous nonwoven structures such as a nonwoven web.

In one embodiment of the present invention, the thermoplastic composition is formed into a fibrous matrix for incorporation into a disposable absorbent product. A fibrous matrix may take the form of, for example, a fibrous nonwoven web. Fibrous nonwoven webs may be made completely from fibers prepared from the thermoplastic composition of the present invention or they may be blended with other fibers. The length of the fibers used may depend on the particular end use contemplated. Where the fibers are to be degraded in water as, for example, in a toilet, it is advantageous if the lengths are maintained at or below about 15 millimeters.

The thermoplastic composition can also be used as a coated or co-extruded component of a flushable film for applications in composite cloth-like outercovers for flushable diapers, or as a baffle barrier film for feminine care napkins and adult incontinence products. These thermoplastic composition can also be used in cast film or blown film applications.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the backsheet comprises fibers prepared from the thermoplastic composition of the present invention.

Disposable absorbent products and structures according to all aspects of the present invention are generally subjected, during use, to multiple insults of a body liquid. Accordingly, the disposable absorbent products and structures are desirably capable of absorbing multiple insults of body liquids in quantities to which the disposable absorbent products and structures will be exposed during use. The insults are generally separated from one another by a period of time.

Test Methods

Apparent Viscosity

A capillary rheometer, under the designation Göttfert Rheograph 2003 capillary rheometer, which was used in combination with WinRHEO (version 2.31) analysis software, both available from Göttfert Company of Rock Hill, S.C., was used to evaluate the apparent viscosity rheological properties of material samples. The capillary rheometer setup included a 2000 bar pressure transducer and a 30 mm length/30 mm active length/1 mm diameter/0 mm height/180° run in angle, round hole capillary die.

If the material sample being tested demonstrates or is known to have water sensitivity, the material sample is dried in a vacuum oven above its glass transition temperature, i.e. above 55 or 60° C. for poly(lactic acid) materials, under a vacuum of at least 15 inches of mercury with a nitrogen gas purge of at least 30 standard cubic feet per hour for at least 16 hours.

Once the instrument is warmed up and the pressure transducer is calibrated, the material sample is loaded incrementally into the column, packing resin into the column with a ramrod each time to ensure a consistent melt during testing. After material sample loading, a 2 minute melt time precedes each test to allow the material sample to completely melt at the test temperature. The capillary rheometer takes data points automatically and determines the apparent viscosity (in Pascal·second) at 7 apparent shear rates (in $second^{-1}$): 50, 100, 200, 500, 1000, 2000, and 5000. When examining the resultant curve it is important that the curve be relatively smooth. If there are significant deviations from a general curve from one point to another, possibly due to air in the column, the test run should be repeated to confirm the results.

The resultant rheology curve of apparent shear rate versus apparent viscosity gives an indication of how the material sample will run at that temperature in an extrusion process. The apparent viscosity value at a shear rate of about 1000 $second^{-1}$ and a temperature of about 200° C. is of specific interest because these are the typical conditions found in commercial fiber spinning extruders.

Weight Average Molecular Weight for Polyester Polymers

A gas permeation chromatography (GPC) method may be used to determine the molecular weight distribution of an polyester polymer, such as poly(lactic acid) polymer, samples.

The GPC is setup with two PLgel Mixed K linear 5 micron, 7.5×300 millimeter analytical columns in series. The column and detector temperatures are 30° C. The mobile phase is HPLX grade tetrahydrofuran (THF). The pump rate is 0.8 milliliters per minute with an injection volume of 25 microliters. Total run time is 30 minutes. It is important to note that new analytical columns must be installed every 4 months, a new guard column every month, and a new in-line filter every month.

Standards of polystyrene polymers, obtained from Aldrich Chemical Co., should be mixed into solvent of dichloromethane (DCM):THF (10:90), both HPLC grade, in order to obtain 1 mg/mL concentrations. Multiple polystyrene standards can be combined in one standard solution provided that their peaks do not overlap when chromatographed. A range of standards of about 687 to 400,000 should be prepared. Examples of standard mixtures with Aldrich polystyrenes of varying molecular weights(in weight average molecular weight-$M_w$) include: Standard 1 (401,340; 32,660; 2,727), Standard 2 (45,730; 4,075), Standard 3 (95,800; 12,860) and Standard 4 (184,200; 24,150; 687).

Next, prepare the stock check standard. Dissolve 10 g of a 200,000 molecular weight poly(lactic acid) polymer standard, to 100 ml of HPLC grade DCM to a glass jar with Teflon lined lid using an orbital shaker (at least 30 minutes). Pour out the mixture onto a clean, dry, glass plate and first allow the solvent to evaporate, then place in a 35° C. preheated vacuum oven and dry for about 14 hrs under a vacuum of 25 mm of Hg. Next, remove the poly(lactic acid) polymer from the oven and cut the film into small strips. Immediately grind the samples using a grinding mill (with a 10 mesh screen) taking care not to add too much sample and causing the grinder to freeze up. Store a few grams of the ground sample in a dry glass jar in a dessicator, while the remainder of the sample can be stored in the freezer in a similar type jar.

It is important to prepare a new check standard prior to the beginning of each new sequence and because the molecular weight is greatly affected by sample concentration great care should be taken in its weighing and preparation. To prepare the check standard weigh out 0.0800 g±0.0025 g of 200,000 $M_w$ poly(lactic acid) polymer reference standard into a clean dry scintillation vial. Then using a volumetric pipet or dedicated repipet, add 2 ml of DCM to the vial and screw the cap on tightly. Allow the sample to dissolve completely. Swirl the sample on an orbital shaker, such as a Thermolyne Roto Mix (type 51300) or similar mixer, if necessary. To evaluate whether is it dissolved hold the vial up to the light at a 45° angle. Turn it slowly and watch the liquid as it flows down the glass. If the bottom of the vial does not appear smooth, the sample is not completely dissolved. It may take the sample several hours to dissolve. Once dissolved, add 18 ml of THF using a volumetric pipet or dedicated repipet, cap the vial tightly and mix.

Sample preparations begins by weighing 0.0800 g±0.0025 g of the sample into a clean, dry scintillation vial (great care should also be taken in its weighing and preparation). Add 2 ml of DCM to the vial with a volumetric pipet or dedicated repipet and screw the cap on tightly. Allow the sample to dissolve completely using the same technique described in the check standard preparation above. Then add 18 ml of THF using a volumetric pipet or dedicated repipet, cap the vial tightly and mix.

Begin the evaluation by making a test injection of a standard preparation to test the system equilibration. Once equilibration is confirmed inject the standard preparations. After those are run, inject the check standard preparation. Then the sample preparations. Inject the check standard preparation after every 7 sample injections and at the end of testing. Be sure not to take any more than two injections from any one vial, and those two injections must be made within 4.5 hours of each other.

There are 4 quality control parameters to assess the results. First, the correlation coefficient of the fourth order regression calculated for each standard should be not less than 0.950 and not more than 1.050. Second, the relative standard deviation (RSD) of all the $M_w$'s of the check standard preparations should not be more than 5.0 percent. Third, the average of the $M_w$'s of the check standard preparation injections should be within 10 percent of the $M_w$ on the first check standard preparation injection. Lastly, record the lactide response for the 200 microgram per milliliter (μg/mL) standard injection on a SQC data chart. Using the chart's control lines, the response must be within the defined SQC parameters.

Calculate the Molecular statistics based on the calibration curve generated from the Polystyrene standard preparations and Mark Houwink constants for PLA and Polystyrene in THF at 30° C. Those are: Polystyrene (K=14.1*10$^5$, alpha=0.700) and PLA (K=54.9*10$^5$, alpha=0.639).

Weight Average Molecular Weight of Polyethylene Oxide

A gas permeation chromatography (GPC) method may be used to determine the weight average molecular weight of polyethylene oxide samples.

A differential refractometer, available from Viscotek Corporation under the designation Knauer Differential Refractometer with a Viscotek Differential Viscometer, Model 100, is set up with two linear, 120 Angstrom Waters Ultrahydrogel gas permeation chromatography columns having a flow rate of about 1.0 ml/minute and an injection volume of 100 microliters. The mobile phase is a 0.05M sodium nitrate aqueous solution. The mobile phase is filtered with a 0.45 micron filter and degassed using a vacuum and an ultrasound bath. Polyethylene oxide standards are obtained having narrow molecular weight distributions with known peak average molecular weight and intrinsic viscosity values.

Samples of both the standard polyethylene oxides and experimental polyethylene oxide materials are prepared by dissolving about 10 to 25 mg (weighed to the nearest 0.0001 g) of a polyethylene oxide material into about 20.0 ml of the mobile phase solution in a clear borosilicate scintillation vial. Each standard and experimental sample is chromotagraphed three times in order to ensure reproducibility of results and to guard against unexpected instrumental upsets. The data is collected and calculated using Unical GPC software, version 4.03, available from Viscotek Corporation of Houston, Tex. The software manual describes in detail all the formulas, algorithms and convolute integrals used for the calculations. For each sample, the weight average molecular weight is obtain.

To confirm that the instrument is operating correctly, a number of checks are performed. The differential refractometer should have a reading of 3.0 millivolts on the detector output, the differential transducers on the viscometer should be set close to zero, and system back pressure should have a reading below 1000 psi. A monodisperse low molecular weight standard peak should be symmetrical and the total number of plates should be above 16,000 plates/bank.

Water Dispersibility/Solubility of a Fiber

The equipment includes a DCA-322 Dynamic Contact Angle Analyzer and WinDCA (version 1.02) software, both available from ATI-CAHN Instruments, Inc., of Madison, Wis. Testing was done on the "A" loop with a balance stirrup attached. Calibrations should be done monthly on the motor and daily on the balance (100 mg mass used) as indicated in the manual.

Thermoplastic compositions are spun into fibers and the freefall sample (jetstretch of 0) is used for the determination of water dispersibility. Care should be taken throughout fiber preparation to minimize fiber exposure to handling to ensure that contamination is kept to a minimum. The fiber sample is attached to a wire hanger with adhesive tape such that about 3 cm of the fiber extends beyond the end of the hanger. The fiber sample is then cut with a razor so that about 2.5 cm is extending beyond the end of the hanger. An optical microscope is used to determine the average diameter (by using 3 to 4 measurements) along the fiber.

The fiber sample on the wire hanger is suspended from the balance stirrup on loop "A". The immersion liquid is distilled water and it is changed for each specimen. The specimen parameters (such as fiber diameter) are entered into the software and the test started. The stage advances at 264 microns/second until it detects the Zero Depth of Immersion, which is when the fiber contacts the surface of the distilled water. From the Zero Depth of Immersion, the fiber advances into the water for 2 cm so the fiber becomes submerged in the liquid. The software then collects force readings over time and the software produces a force versus time plot of this data.

The data analysis is based on the force versus time plot. The specific point of interest in this plot is the maximum force point, if it exists, known as the "onset" point. This change in force resulting in the peak, or maximum force point, reflects the change from water absorption/uptake to water dissolution. "Instant" solubility is that where the onset point occurs at less than about 5 minutes. "Delayed" solubility is when the onset point occurs at a time greater than about 5 minutes but less than about 2 hours. A fiber sample is "Insoluble" when no onset point occurs within a time less than about 2 hours.

EXAMPLES

Example 1

Bicomponent fibers with a 1:1 core to sheath extruder throughput weight ratio structure were prepared by using various thermoplastic compositions as the sheath material and a polypropylene as the core material. The polypropylene used was obtained from HIMONT USA, Inc. located at Wilmington, Del., under the designation PF305 polypropylene, exhibiting a melting temperature of about 165° C.

The fiber spinning was done on a bicomponent spinning line consisting of two similar extruders, each having a 0.75 inch diameter and a 24:1 L:D (length:diameter) ratio screw and 3 heating zones which feeds into a spin pump, through a 0.62 inch Koch® SMX static mixer unit and then into a sheath/core bicomponent spin pack (representing the 4$^{th}$ and 5$^{th}$ heating zones), from which fibers are spun through 16 holes of about 300 micrometers diameter.

The extruder temperature profile for the sheath in the five different zones is listed in Table 1 and the extruder temperature for the core in the five different zones is 150° C./166° C./175° C./190° C./190° C. The fiber was quenched down to 15° C. and drawn down to where it was either formed into a nonwoven or collected for further processing (such as crimping and cutting for production of staple and short-cut fibers) before being formed into a nonwoven.

The following thermoplastic compositions were used as sheath materials:

Sample 1: A polyethylene oxide, obtained from Union Carbide Corporation of Danbury, Conn., under the designation POLYOX® WSRN-80 polyethylene oxide, which had a melting temperature of about 64° C., a melt flow at about 190° C. and 21.6 kilograms of between 25 to 35 grams/minute, and a reported weight average molecular weight of about 200,000, was used in a weight percent of 100 weight percent.

Sample 2: A poly(lactic acid) polymer, obtained from Chronopol Inc., Golden, Colo. under the designation CPX5-1 poly(lactic acid) polymer, which had a melting temperature of about 175° C., an L:D ratio of 100:0, a weight average molecular weight of about 215,000, a number average molecular weight of about 127,000, a polydispersity index of about 1.66, and a residual lactic acid monomer amount of less than about 3 weight percent, was used in a weight percent of about 47 weight percent. POLYOX® WSRN-80 polyethylene oxide was used in a weight percent of about 47 weight percent. An ethylene oxide and caprolactone copolymer, available from Union Carbide Corporation of Bound Brook, N.J., under the designation TONE® P303 ethylene oxide and caprolactone copolymer and having a melting temperature of about 60° C. and a number average molecular weight of about 41,000, was used in a weight percent of about 6 weight percent.

Sample 3: A poly(lactic acid) polymer, obtained from Chronopol Inc., Golden, Colo., under the designation CPX5-2 poly(lactic acid) polymer, which had a melting temperature of about 140° C., an L:D ratio of about 95 to 5, a weight average molecular weight of about 190,000, a number average molecular weight of about 108,000, a polydispersity index of about 1.74, and a residual lactic acid monomer amount of about 4.8 weight percent, was used in a weight percent of about 50 weight percent. POLYOX® WSRN-80 polyethylene oxide was used in a weight percent of about 50 weight percent.

Sample 4: Himont PF305 polypropylene was used in a weight percent of about 50 weight percent. POLYOX® WSRN-80 polyethylene oxide was used in a weight percent of about 50 weight percent.

Sample 5: CPX5-1 poly(lactic acid) polymer was used in a weight percent of about 50 weight percent. Himont PF305 polypropylene was used in a weight percent of about 50 weight percent.

Sample 6: A polyethylene polymer, obtained from The Dow Chemical Company, Midland, Mich., under the designation ASPUN® PE6811A polyethylene polymer and having a melting temperature of about 130° C., was used in a weight percent of 100 weight percent.

Sample 7: CPX5-2 poly(lactic acid) polymer was used in a weight percent of about 100 weight percent.

Sample 8: CPX5-2 poly(lactic acid) polymer was used in a weight percent of about 25 weight percent. POLYOX® WSRN-80 polyethylene oxide was used in a weight percent of about 58 weight percent. ASPUN® PE6811A polyethylene polymer was used in a weight percent of about 17 weight percent.

Sample 9: CPX5-2 poly(lactic acid) polymer was used in a weight percent of about 22 weight percent. POLYOX® WSRN-80 polyethylene oxide was used in a weight percent of about 51 weight percent. ASPUN® PE6811A polyethylene polymer was used in a weight percent of about 17 weight percent. A compatibilizer, obtained from Petrolite Corporation of Tulsa, Okla., under the designation UNITHOX®480 ethoxylated alcohol and having a melting temperature of about 64° C. and a number average molecular weight of about 2250, was used in a weight percent of about 11 weight percent.

Sample 10: CPX5-2 poly(lactic acid) polymer was used in a weight percent of about 36 weight percent. POLYOX® WSRN-80 polyethylene oxide was used in a weight percent of about 36 weight percent. ASPUN® PE6811A polyethylene polymer was used in a weight percent of about 17 weight percent. UNITHOX®480 ethoxylated alcohol was used in a weight percent of about 11 weight percent.

When more than one component was used, a blend of the various components for a particular sample involved dry mixing the components followed by melt mixing them together to provide vigorous mixing of the components, which was achieved in a counter-rotating twin screw extruder. Mixing was conducted on either a Brabender twin screw compounder or a Haake twin screw extruder with mixing screws.

The temperature profile process conditions, evaluations for Apparent Viscosity values and water dispersibility, and comments on the processability of the prepared fibers are shown in Table 1.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

TABLE 1

| Sample No. | Apparent Viscosity (Pa · s) (at 200° C., 1000 s$^{-1}$) | Sheath Extruder Processing Temperature (° C.) Profile | Fiber Drawability | Fiber Processability Comments | Water Dispersibility |
| --- | --- | --- | --- | --- | --- |
| *Sample 1 | 366 | 160/175/175/175/175 | Can not be drawn down | Strong elastic retraction behavior and poor melt strength. | Instant |
| *Sample 2 | 206 | 175/180/185/185/185 | Can not be drawn down | Strong elastic retraction behavior and poor melt strength | Delayed |
| *Sample 3 | 219 | 150/160/160/170/170 | Can not be drawn down | Strong elastic retraction behavior and poor melt strength. | Delayed |
| *Sample 4 | 232 | 160/175/175/175/175 | Can not be drawn down | Poor melt strength, fiber breaks often | Delayed |
| *Sample 5 | 110 | 180/200/190/190/190 | Can be drawn down to 50 m/min | Poor melt strength, fiber breaks often | Insoluble |
| *Sample 6 | 40 | 120/130/140/155/155 | Can be drawn down | Good melt strength | Insoluble |

TABLE 1-continued

| Sample No. | Apparent Viscosity (Pa · s) (at 200° C., 1000 s$^{-1}$) | Sheath Extruder Processing Temperature (° C.) Profile | Fiber Drawability | Fiber Processability Comments | Water Dispersibility |
|---|---|---|---|---|---|
| *Sample 7 | 125 | 180/207/198/198/198 | Can be drawn down to over 100 m/min 50 m/min | Better melt strength than PEO control but limited draw down. | Insoluble |
| Sample 8 | 136.8 | 150/160/170/180/180 | Can be drawn down to 50 m/min | Better melt strength than PEO control but limited draw down. | Delayed |
| Sample 9 | 65.1 | 140/160/170/180/180 | Can be drawn down to 50 m/min | Better melt strength than PEO control but limited draw down. | Delayed |
| Sample 10 | 45.6 | 140/160/170/180/180 | Can be drawn down to 100 m/min | Melt strength allows for typical drawing down. | Delayed |

*Not an example of the present invention.

What is claimed is:

1. A thermoplastic composition comprising a mixture of:
   a. a polyethylene oxide polymer having a weight average molecular weight that is between about 100,000 to about 20,000,000, wherein the polyethylene oxide polymer is present in the thermoplastic composition in a weight amount that is between about 5 weight percent to about 60 weight percent;
   b. a polyolefin polymer, wherein the polyolefin polymer is present in the thermoplastic composition in a weight amount that is between about 5 weight percent to about 40 weight percent;
   c. a polyester polymer having a weight average molecular weight that is between about 10,000 to about 2,000,000, wherein the polyester polymer is present in the thermoplastic composition in a weight amount that is between about 5 weight percent to about 70 weight percent, wherein all weight percents are based on the total weight amount of the polyethylene oxide polymer, the polyester polymer and the polyolefin polymer present in the thermoplastic composition; and
   d. a compatibilizer that exhibits a hydrophilic-lipophilic balance ratio that is between about 10 to about 40, wherein the compatibilizer is present in the thermoplastic composition in a weight amount that is greater than about 0 weight percent to about 25 weight percent;
   wherein the thermoplastic composition exhibits an Apparent Viscosity value at a temperature of about 200° C. and a shear rate of about 1000 seconds$^{-1}$ that is between about 5 Pascal seconds to about 200 Pascal seconds.

2. The thermoplastic composition of claim 1 wherein the compatibilizer is an ethoxylated alcohol.

3. The thermoplastic composition of claim 1 wherein the polyolefin polymer is selected from the group consisting of polyethylene and polypropylene.

4. The thermoplastic composition of claim 1 wherein the polyester polymer is selected from the group consisting of poly(lactic acid), polybutylene succinate, polybutylene succinate-co-adipate, polyhydroxybutyrate-co-valerate, polycaprolactone, sulfonated polyethylene terephthalate, mixtures of such polymers, and copolymers of such polymers.

5. The thermoplastic composition of claim 4 wherein the polyester polymer is poly(lactic acid).

6. The thermoplastic composition of claim 1 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

7. The thermoplastic composition of claim 1 wherein the polyethylene oxide polymer is present in the thermoplastic composition in a weight amount that is between about 10 weight percent to about 55 weight percent, the polyolefin polymer is present in the thermoplastic composition in a weight amount that is between about 10 weight percent to about 35 weight percent, and the polyester polymer is present in the thermoplastic composition in a weight amount that is between about 10 weight percent to about 60 weight percent.

8. The thermoplastic composition of claim 1 wherein the polyolefin polymer is selected from the group consisting of polyethylene and polypropylene and the polyester polymer is poly(lactic acid).

9. The thermoplastic composition of claim 1 wherein the thermoplastic composition, when immersed in water, exhibits a maximum force point that occurs at a time greater than about 5 minutes but less than about 2 hours.

10. A fiber prepared from a thermoplastic composition, the thermoplastic composition comprising a mixture of:
    a. a polyethylene oxide polymer having a weight average molecular weight that is between about 100,000 to about 20,000,000, wherein the polyethylene oxide polymer is present in the thermoplastic composition in a weight amount that is between about 5 weight percent to about 60 weight percent;
    b. a polyolefin polymer, wherein the polyolefin polymer is present in the thermoplastic composition in a weight amount that is between about 5 weight percent to about 40 weight percent; and
    c. a polyester polymer having a weight average molecular weight that is between about 10,000 to about 2,000,000, wherein the polyester polymer is present in the thermoplastic composition in a weight amount that is between about 5 weight percent to about 70 weight percent, wherein all weight percents are based on the total weight amount of the polyethylene oxide polymer, the polyester polymer and the polyolefin polymer present in the thermoplastic composition;
    wherein the thermoplastic composition exhibits an Apparent Viscosity value at a temperature of about 200° C. and a shear rate of about 1000 seconds$^{-1}$ that is between about 5 Pascal seconds to about 200 Pascal seconds.

11. The fiber of claim 10 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

12. The fiber of claim 11 wherein the compatibilizer is an ethoxylated alcohol.

13. The fiber of claim 10 wherein the polyolefin polymer is selected from the group consisting of polyethylene and polypropylene.

14. The fiber of claim 10 wherein the polyester polymer is selected from the group consisting of poly(lactic acid), polybutylene succinate, polybutylene succinate-co-adipate, polyhydroxybutyrate-co-valerate, polycaprolactone, sulfonated polyethylene terephthalate, mixtures of such polymers, and copolymers of such polymers.

15. The fiber of claim 14 wherein the polyester polymer is poly(lactic acid).

16. The fiber of claim 10 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

17. The fiber of claim 10 wherein the polyethylene oxide polymer is present in the thermoplastic composition in a weight amount that is between about 10 weight percent to about 55 weight percent, the polyolefin polymer is present in the thermoplastic composition in a weight amount that is between about 10 weight percent to about 35 weight percent, and the polyester polymer is present in the thermoplastic composition in a weight amount that is between about 10 weight percent to about 60 weight percent.

18. The fiber of claim 17 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

19. The fiber of claim 17 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

20. The fiber of claim 10 wherein the polyolefin polymer is selected from the group consisting of polyethylene and polypropylene and the polyester polymer is poly(lactic acid).

21. The fiber of claim 20 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

22. The fiber of claim 21 wherein the compatibilizer is an ethoxylated alcohol.

23. The fiber of claim 21 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

24. The fiber of claim 10 wherein the fiber, when immersed in water, exhibits a maximum force point that occurs at a time greater than about 5 minutes but less than about 2 hours.

25. A disposable absorbent product comprising a liquid-permeable topsheet, a backsheet attached to the liquid-permeable topsheet, and an absorbent structure positioned between the liquid-permeable topsheet and the backsheet, wherein the backsheet comprises fibers prepared from a thermoplastic composition comprising a mixture of:

a. a polyethylene oxide polymer having a weight average molecular weight that is between about 100,000 to about 20,000,000, wherein the polyethylene oxide polymer is present in the thermoplastic composition in a weight amount that is between about 5 weight percent to about 60 weight percent;

b. a polyolefin polymer, wherein the polyolefin polymer is present in the thermoplastic composition in a weight amount that is between about 5 weight percent to about 40 weight percent; and c. a polyester polymer having a weight average molecular weight that is between about 10,000 to about 2,000,000, wherein the polyester polymer is present in the thermoplastic composition in a weight amount that is between about 5 weight percent to about 70 weight percent, wherein all weight percents are based on the total weight amount of the polyethylene oxide polymer, the polyester polymer and the polyolefin polymer present in the thermoplastic composition;

wherein the thermoplastic composition exhibits an Apparent Viscosity value at a temperature of about 200° C. and a shear rate of about 1000 seconds$^{-1}$ that is between about 5 Pascal seconds to about 200 Pascal seconds.

26. The disposable absorbent product of claim 25 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

27. The disposable absorbent product of claim 26 wherein the compatibilizer is an ethoxylated alcohol.

28. The disposable absorbent product of claim 25 wherein the polyolefin polymer is selected from the group consisting of polyethylene and polypropylene.

29. The disposable absorbent product of claim 25 wherein the polyester polymer is selected from the group consisting of poly(lactic acid), polybutylene succinate, polybutylene succinate-co-adipate, polyhydroxybutyrate-co-valerate, polycaprolactone, sulfonated polyethylene terephthalate, mixtures of such polymers, and copolymers of such polymers.

30. The disposable absorbent product of claim 29 wherein the aliphatic polyester polymer is poly(lactic acid).

31. The disposable absorbent product of claim 25 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

32. The disposable absorbent product of claim 25 wherein the polyethylene oxide polymer is present in the thermoplastic composition in a weight amount that is between about 10 weight percent to about 55 weight percent, the polyolefin polymer is present in the thermoplastic composition in a weight amount that is between about 10 weight percent to about 35 weight percent, and the polyester polymer is present in the thermoplastic composition in a weight amount that is between about 10 weight percent to about 60 weight percent.

33. The disposable absorbent product of claim 32 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

34. The disposable absorbent product of claim 33 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

35. The disposable absorbent product of claim 25 wherein the polyolefin polymer is selected from the group consisting of polyethylene and polypropylene and the polyester polymer is poly(lactic acid).

36. The disposable absorbent product of claim 35 wherein the thermoplastic composition further comprises a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

37. The disposable absorbent product of claim 36 wherein the compatibilizer is an ethoxylated alcohol.

38. The disposable absorbent product of claim 35 wherein the thermoplastic composition exhibits an Apparent Viscosity value at a temperature of about 200° C. and a shear rate of about 1000 seconds$^{-1}$ that is between about 10 Pascal seconds to about 150 Pascal seconds.

39. The disposable absorbent product of claim 25 wherein the fiber, when immersed in water, exhibits a maximum force point that occurs at a time greater than about 5 minutes but less than about 2 hours.

40. A thermoplastic composition comprising a mixture of:
   a. a polyethylene oxide polymer having a weight average molecular weight that is between about 100,000 to about 20,000,000, wherein the polyethylene oxide polymer is present in the thermoplastic composition in a weight amount that is between about 5 weight percent to about 60 weight percent;
   b. a polyolefin polymer, wherein the polyolefin polymer is present in the thermoplastic composition in a weight amount that is between about 5 weight percent to about 40 weight percent, the polyolefin polymer comprising polyethylene, polypropylene, or a combination thereof; and
   c. an aliphatic polyester polymer having a weight average molecular weight that is between about 10,000 to about 2,000,000, wherein the aliphatic polyester polymer comprises poly(lactic acid) and is present in the thermoplastic composition in a weight amount that is between about 5 weight percent to about 70 weight percent, wherein all weight percents are based on the total weight amount of the polyethylene oxide polymer, the aliphatic polyester polymer and the polyolefin polymer present in the thermoplastic composition;

wherein the thermoplastic composition exhibits an Apparent Viscosity value at a temperature of about 200° C. and a shear rate of about 1000 seconds$^{-1}$ that is between about 5 Pascal seconds to about 200 Pascal seconds.

41. The thermoplastic composition of claim 40, further comprising:
   d. a compatibilizer that exhibits a hydrophilic-lipophilic balance ratio that is between about 10 to about 40, wherein the compatibilizer is present in the thermoplastic composition in a weight amount that is between about 0 weight percent to about 25 weight percent.

42. The thermoplastic composition of claim 41, wherein the compatibilizer comprises ethoxylated alcohol.

43. The thermoplastic composition of claim 40, wherein the thermoplastic composition, when immersed in water, exhibits a maximum force point that occurs at a time greater than about 5 minutes and less than about 2 hours.

44. A fiber formed from the thermoplastic composition of claim 40.

45. A disposable absorbent product comprising the thermoplastic composition of claim 40.

* * * * *